(12) United States Patent
Lee et al.

(10) Patent No.: US 7,951,395 B2
(45) Date of Patent: May 31, 2011

(54) DERMAL APPLICATION SYSTEM FOR AMINOLAEVULINIC ACID

(75) Inventors: Geoffrey Lee, Neunkirchen am Brand (DE); Rolf-Markus Szeimies, Zeitlarn (DE)

(73) Assignee: Photonamic GmbH & Co. KG, Hamburg (DE)

( * ) Notice: Subject to any disclaimer, the term of this patent is extended or adjusted under 35 U.S.C. 154(b) by 1133 days.

(21) Appl. No.: 10/332,547

(22) PCT Filed: Jul. 13, 2001

(86) PCT No.: PCT/EP01/08131
§ 371 (c)(1),
(2), (4) Date: Sep. 30, 2003

(87) PCT Pub. No.: WO02/05809
PCT Pub. Date: Jan. 24, 2002

(65) Prior Publication Data
US 2005/0013852 A1    Jan. 20, 2005

(30) Foreign Application Priority Data

Jul. 17, 2000  (DE) .................................. 100346731

(51) Int. Cl.
*A61F 13/00*  (2006.01)
*A61K 9/14*  (2006.01)

(52) U.S. Cl. ........ 424/449; 424/447; 424/448; 424/486; 424/487; 424/489

(58) Field of Classification Search .................. 424/489, 424/447, 449
See application file for complete search history.

(56) References Cited

U.S. PATENT DOCUMENTS

| 5,456,745 | A   | * | 10/1995 | Roreger et al. ............ 106/140.1 |
| 5,520,905 | A   |   | 5/1996  | Uhlmann et al. |
| 5,856,566 | A   | * | 1/1999  | Golub ........................... 562/567 |
| 6,280,765 | B1  | * | 8/2001  | Gueret .......................... 424/449 |
| 7,176,242 | B2  |   | 2/2007  | John et al. ..................... 514/615 |
| 2004/0171881 | A1 |  | 9/2004  | John et al. |
| 2006/0018956 | A1 |  | 1/2006  | Lee et al. |

FOREIGN PATENT DOCUMENTS

| EP | 0704209 A | 4/1996 |
| WO | WO 94/06424 | 3/1994 |
| WO | WO 95/05813 A | 3/1995 |
| WO | WO 95/07077 A | 3/1995 |
| WO | WO 96/06602 A | 3/1996 |
| WO | WO 97/10811 | 3/1997 |
| WO | WO 98/30242 A | 7/1998 |
| WO | WO 99/11604 A | 3/1999 |
| WO | WO 00/28971 A | 5/2000 |
| WO | WO 02/05809 | 1/2002 |

OTHER PUBLICATIONS

Kennedy et al., "Photodynamic therapy with endogenous protoporphyrin IX: basic principles and present clinical experience,", *J Photochem Photobiol B*, Jun. 6, 1990 (1-2):143-148.

Rodriguez et al., "Chemical instability of 5-aminolevulinic acid (ALA) in aqueous solution," *Proc. SPIE, 5th International Photodynamic Association Biennial Meeting*, 1995, 2371:204-209.

(Continued)

*Primary Examiner* — Lakshmi S Channavajjala
(74) *Attorney, Agent, or Firm* — Pabst Patent Group LLP

(57) ABSTRACT

The invention relates to a dermal for aminolaevulinic acid, wherein a self-adhesive matrix system is used containing crystalline aminolaevulinic acids.

5 Claims, 9 Drawing Sheets

Comparison of ALA release/permeation through excised human skin membrane, from the NE/ATBC (1:2) patch system (10 wt.% ALA load) directly after production and after 6 months' storage.

Key:
● after 24 hours, freshly produced patch
■ after 6 months' storage

OTHER PUBLICATIONS

Sugibayashi et al., "Polymers for transdermal drug delivery systems," *J Control Rel*, 1994, 29:177-185.

Tojo, K.; 'Design and Calibration of in Vitro Permeation Apparatus•; Transdermal Controlled Systemic Medication, Marcel Deckker,(1987); pp. 127-158.

Peterson, et al.; "Design, Development, Manufacturing, and Testing of Transdermal Drug Delivery Systems"; Transdermal and Topical Drug Delivery Systems, Faram Press (1997), Buffalo Grove, IL/USA; pp. 249-297.

Dittgen, P.; "Transdermate TherapeutischeSysteme"; Pharmazeutische Thechnotogies: Modeme Arzneiformem; Wissenschaftliche Verlagsgesellschaft Stuttgart (1997); pp. 133-156.

U.S. Appl. No. 10/502,495, filed Jun. 24, 2005, Lee, et al.

445. δ-Aminolevulinic Acid 2001 The Merck Index,Thirteenth Edition. Merck Research Laboratories, p. 78.

Wynn, R.W., Corwin, A.H. 1950 The Hydrogenation of Oxaloacetone. A New Synthesis of β-Thiolimidazolylpropionic Acid. J. Org. Chem. 15:203-208.

Marei, A.A., Raphael, R.H. 1958 The Synthesis of Amino-acids from Furfurylamine. J. Chem. Soc. 2624-26.

Herdeis, C., Dimmerlung, A. 1984 Eine dreistufige Synthese der δ-Aminolaevulinsaure. Arch. Pharm. 317:304-306.

A5, 990-5 5-Aminolevulinic acid hydrochloride. 2000-2001 Aldrich Handbook of Fine Chemicals and Laboratory Equipment. p. 83.

* cited by examiner

Fig. 1: Comparison of ALA release/permeation through excised human skin membrane, from the NE/ATBC (1:2) patch system (10 wt.% ALA load) directly after production and after 6 months' storage.
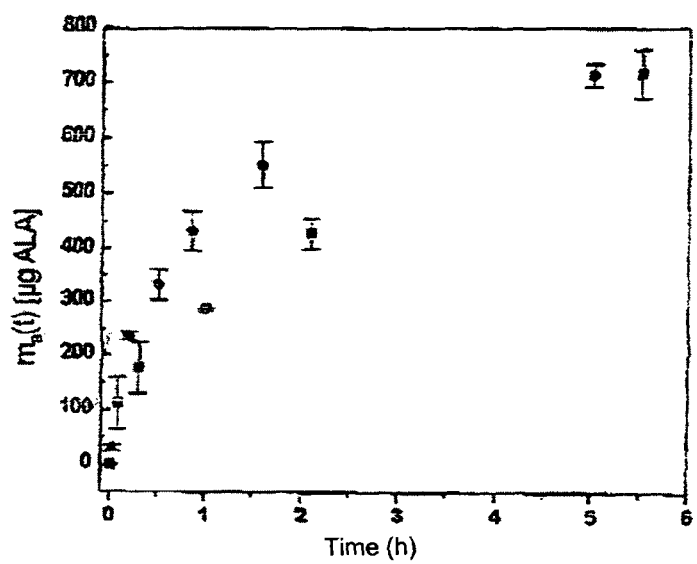
Key:
● after 24 hours, freshly produced patch
■ after 6 months' storage Fig. 2: Fluorescence from patch (Eudragit NE/acetyl tributyl citrate 1:1) 20% loaded with ALA, application time 3 hours

Fig. 3 Release profile of ALA from the NE/ATBC (1:2.5) patch
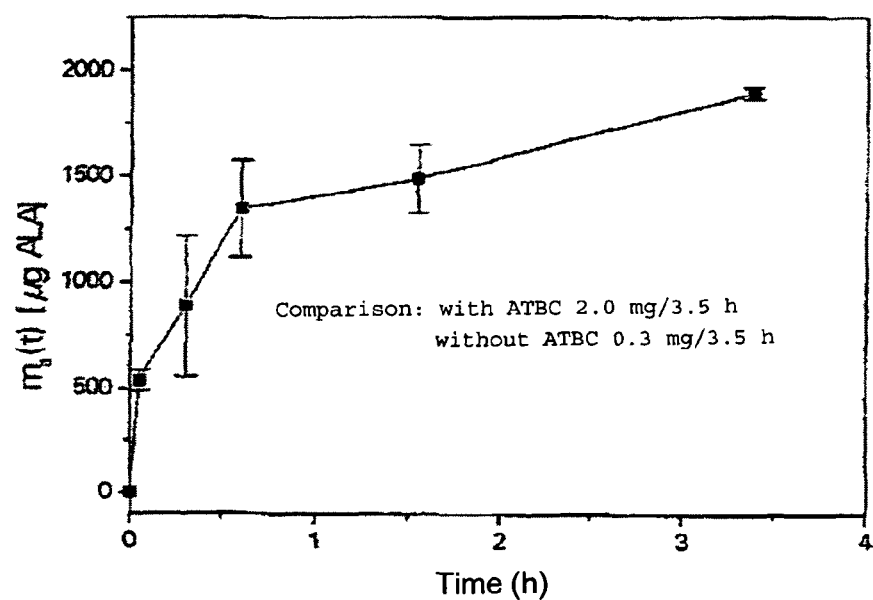

Fig. 4: Scanning Electron Micrograph of the surface of a patch loaded with 50% g/g ALA (NE/ATBC (1:1.5), film thickness 250 µm, sieve fraction 90-160µm).
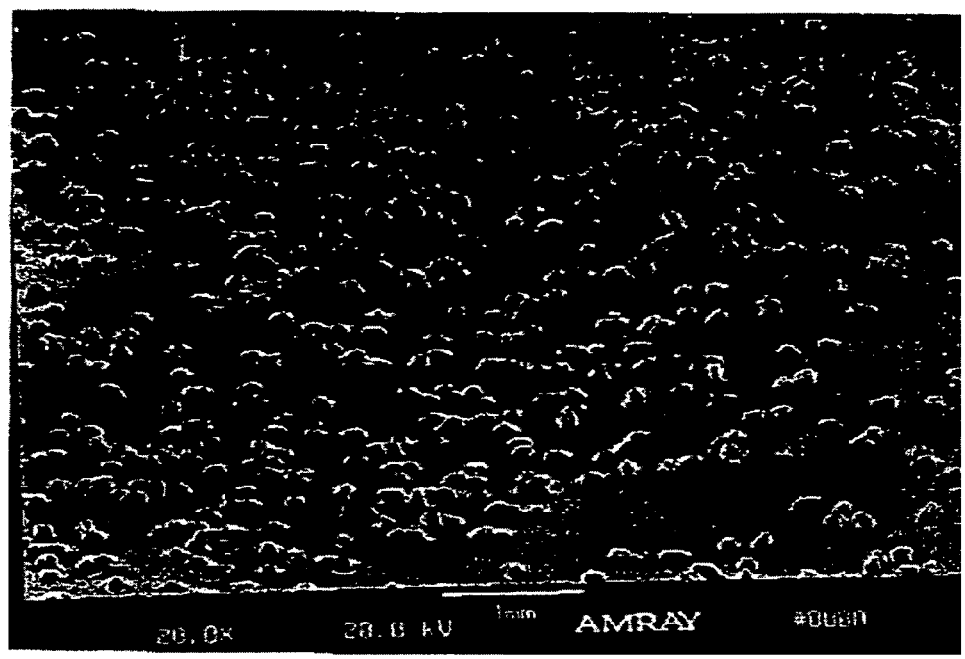

Fig. 5: Scanning Electron Micrograph of the surface of a patch loaded with 50% g/g ALA (NE/ATBC (1:1.5), film thickness 250 µm, sieve fraction 90-160µm) after 1 minute's contact with water.
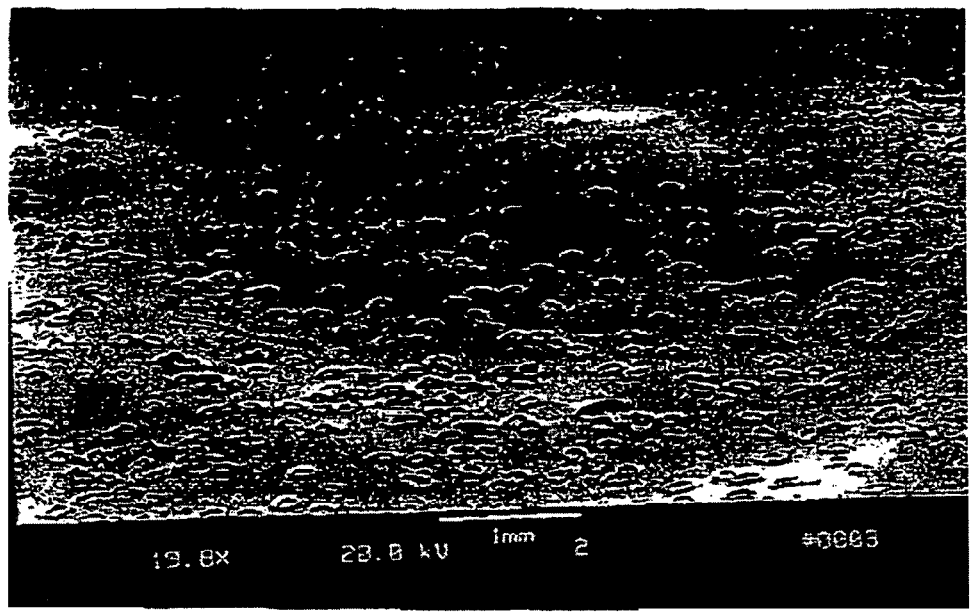

Fig. 6: Release/permeation profile of ALA from the NE/ATBC (1:2) suspension patch through excised human stratum corneum/epidermis.
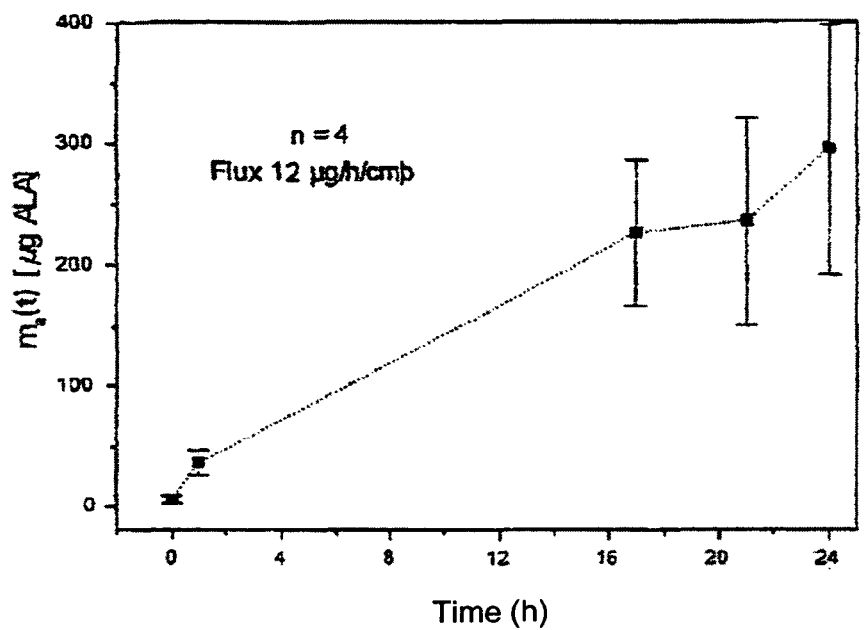

Fig. 7: Release/permeation profile of ALA from the ointment base Psoralon-Fettcreme® (contains 10 wt.% ALA) through excised human stratum corneum/epidermis.
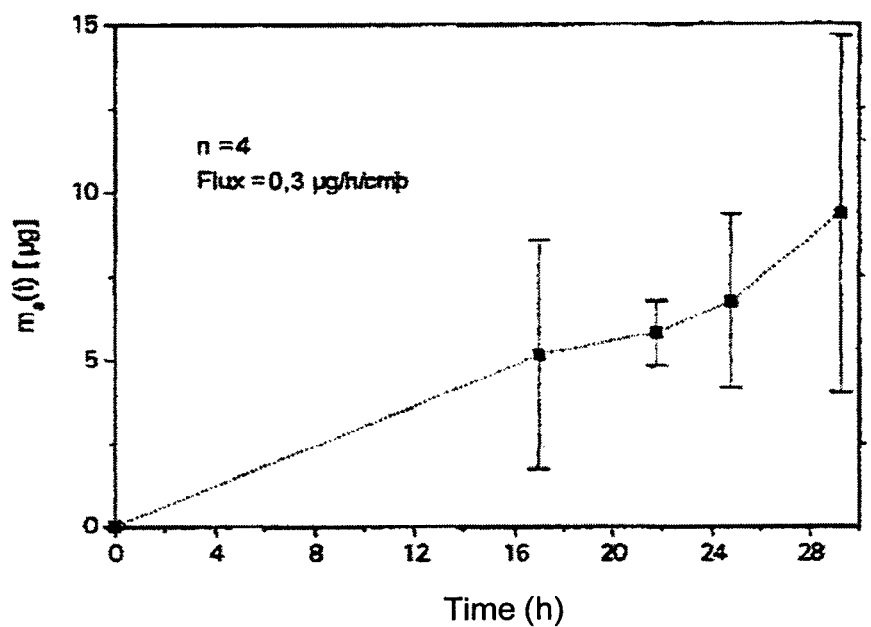

Fig. 8: Release/permeation profile of ALA from hydroxyethyl cellulose gel (contains 10 wt.% ALA) through excised human stratum corneum/epidermis.
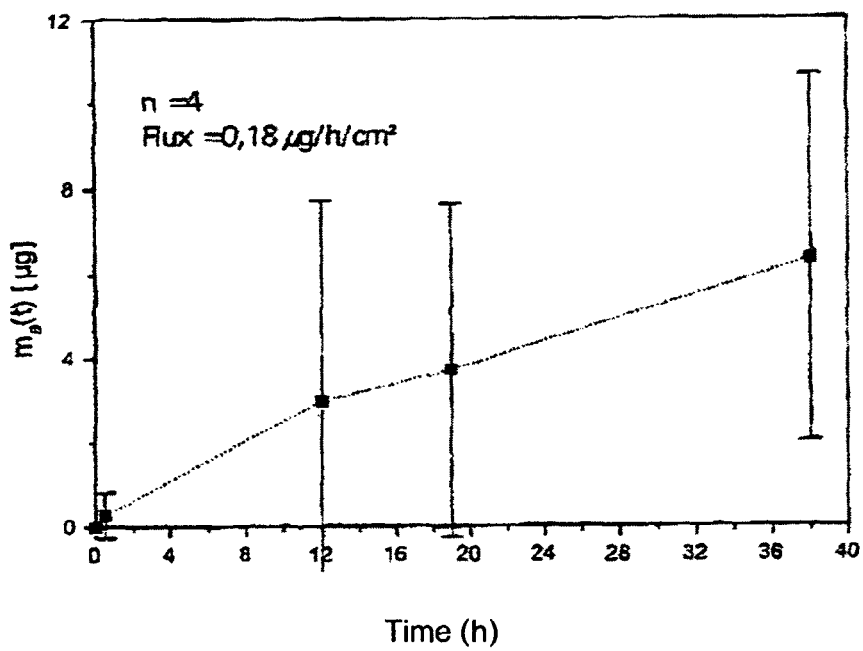

Fig. 9 Fluorescence intensity depending on the duration application for dermal application system in comparison with Psoralon-Fettcreme.
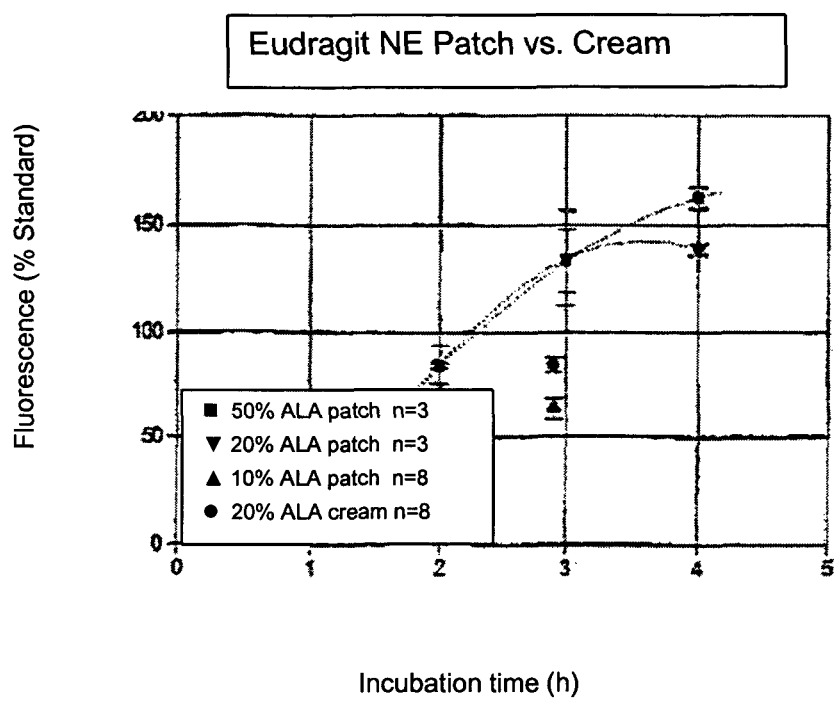

DERMAL APPLICATION SYSTEM FOR AMINOLAEVULINIC ACID

The invention relates to a dermal application system for aminolaevulinic acid.

The topical use of 5-aminolaevulinic acid (ALA) (δ-ALA) in the treatment of superficial skin tumours, in particular basaliomas, was first described in 1990 by Kennedy et al. (J. Photochem. Photobiol. B. 6 (1990) 143-148), wherein primarily visually recognisable tumours are locally brought into contact with ALA. ALA is selectively absorbed and accumulated by tumour tissue, so that it leads to increased porphyrin formation and concentration only there, whilst the healthy tissue remains essentially unaffected. The effect of ALA is based on stimulation of the body's own porphyrin formation. As the porphyrin fluoresces strongly when irradiated, the ALA-/porphyrin accumulation in the tumour tissue can be utilised for diagnosis of pre-cancerous and cancerous lesions and for photodynamic therapy of tumour diseases.

The pharmaceutical formulation of ALA preparations is subject to practical limitations due to the instability of ALA in aqueous solution. Thus, at a very low pH value, ALA proves to be sufficiently stable, but as the pH-value increases, the stability declines steadily (cf. Rodriguez et al., S.P.I.E. (Society of Photo-optical Instrumentation Engineers) 2371 (1995) 204-209). A fresh ALA solution for example, at an approximate physiological value of 8, after just two weeks has only approx. 10% of undecomposed active substance. For this reason, ready-to-use ALA preparations such as solutions and ointments are not commercially available, but have to be prepared fresh, starting from pure ALA, immediately before application, and will then keep for a very limited period, typically less than two weeks.

EP 0 704 209 A1 relates to ALA-containing compositions in particular in the form of gels, emulsions and the like, with the disadvantages described above.

WO95/05813 and WO96/06602 disclose compositions for dermal application of ALA, which have a comparatively low release speed for the active substance.

An object of the present invention is therefore to provide an ALA-preparation which is in the form of a ready-to-use formulation and has storage stability with minimised decomposition of the ALA.

The problem is solved by the dermal application system of the present invention. This system is a self-adhesive matrix system, whose polymer matrix contains crystallinic aminolaevulinic acid in the particle size range of less than approx. 200 μm.

Within the framework of the present invention, it has surprisingly been established, that a rapid release of the ALA is not adversely affected by the choice of the self-adhesive polymer matrix. Due to the selected crystal size range, the sedimentation of the ALA crystals is prevented, and a homogenous ALA distribution predominates in the matrix.

Possible dermal application systems include the PSA-type matrix systems (PSA: Pressure-Sensitive Adhesive) known hitherto, as described, e.g. in Sugibayashi et al., J. Control. Rel. 29 (1994) 177-185 (cf. in particular FIGS. 1a and 1e), or in the monograph "*Pharmazeutische Technologie, Moderne Arzneiformen*" [Pharmaceutical Technology, Modern Drug Forms] (Chapter on "*Transdermale Therapeutische Systeme*" [Transdermal Therapeutic Systems], M. Dittgen; Publisher: R. Müller, G. Hildebrand, Wissenschaftliche Verlagsgesellschaft Stuttgart, 1997).

The application system according to the invention preferably contains a water-permeable polymer matrix, which especially preferably is only partially water-permeable.

The self-adhesive polymer matrix is preferably formed from polymers of the group consisting of
 a) acrylates,
 b) silicon polymers and
 c) polyisobutylene,
which optionally contains softeners, such as e.g. citric acid esters (e.g. acetyl tributyl citrate, ATBC).

For the choice of matrices, polymers are preferred, which have only low solubility vis-à-vis ALA, such as e.g. ethyl acrylate-methyl methacrylate-copolymerisate (Eudragit® NE). Also advantageous is adequate adhesiveness, which makes it possible to produce self-adhesive matrix systems, which can be achieved by the addition of softeners (such as e.g. ATBC).

As a self-adhesive polymer matrix, Eudragit® NE (NE) with acetyl tributyl citrate (ATBC) as softener is especially preferred, in particular in the NE/ATBC mass ratio of 1:0.5 to 1:2.5.

Within the framework of the present invention, it has been shown that ALA crystals with a (mean) diameter of less than 200 μm, preferably 20 to 200 μm, especially preferably 30 to 190 μm, are particularly advantageous. ALA crystals with a diameter of 90 to 160 μm are most preferred.

In the dermal application system according to the invention, ALA is preferably used in a concentration of up to 50 wt. %, in particular of at least 1 wt. % relative to the ready-to-use polymer matrix. An ALA concentration of approximately 20 wt. % is especially preferred.

An embodiment of the invention which is particularly preferred according to the invention, relates to an application system in which ALA crystals possess a diameter of 90 to 160 μm, and the polymer matrix consists of Eudragit® NE (NE) and acetyl tributyl citrate (ATBC) in the NE/ATBC weight ratio of 1:0.5 to 1:2.5, ALA being present in a concentration of up to 50 wt. % relative to the ready-to-use polymer matrix.

The invention further relates to a method for the production of this application system, wherein freeze-dried Eudragit® NE (NE) with acetyl tributyl citrate (ATBC) is dissolved in acetone, in the NE/ATBC mass ratio of 1:0.5 to 1:2.5, after which ground aminolaevulinic acid in the particle size range of 90 to 160 μm is dispersed in the acetone solution, and the dispersion thus obtained is drawn to produce a thin film on a carrier (cover foil), and dried for 45 minutes at 60° C.

The application system hereby provided is characterised in particular by the fact that ALA, in contrast to active substances of conventional patch systems/transdermal application systems, is released very rapidly and can penetrate the skin. On the basis of existing data and knowledge of the field of transdermal therapeutic systems, the high release speed was no more foreseeable than the extremely high storage stability and the long storage duration thus made possible (i.e. storability with minimum decomposition of ALA).

According to a particular embodiment of the invention, at least 30% of the ALA dispersed/suspended in the polymer matrix is released by the application system within 30 minutes. Due to this rapid release of active substance, the time needed for the application system to take effect can be reduced in comparison with conventional applications by means of ointments or cremes, i.e. the contact time of the dermal application system is clearly shorter than the application duration of ALA-containing ointments and cremes used hitherto, to apply the same quantity of active substance. In comparison with the ointments or cremes mentioned, the application system further has the advantage that ALA can be applied to a sharply delimited area of skin in a targeted manner, whilst the application forms used hitherto in the state of the art do not allow this, and penetration of surrounding regions of skin can therefore result.

With the dermal application system of the present invention, a stable ready-to-use preparation of ALA is thus made available for the first time, which even after storage for a period ranging from a few weeks to several months, shows no essential decomposition of ALA. As was surprisingly found, in the system according to the invention, immediately after production and after six months' storage at 25° C., there are no essential differences as regards release of the active substance and skin penetration in vitro or in vivo.

The application system mentioned is thus particularly suitable for use in photodynamic therapy and/or diagnosis of pre-cancerogenic or carcinogenic skin lesions, in particular of skin tumours (basaliomas). The present invention is described below with reference to examples.

EXAMPLES

Example 1

Production of a dermal application system according to the invention:

The patch production can be carried out by means of "Solvent Evaporation", "Hot Melt", or other suitable methods (cf. e.g. T. Peterson et al., "*Design, Development, Manufacturing and Testing of Transdermal Drug Delivery Systems*" in "*Transdermal and Topical Drug Delivery Systems*"; T. Ghosh and W. Pfister, Ed.; Interpharm Press 1997, Buffalo Grove, Ill./USA). This is to be illustrated with reference to the "Solvent Evaporation" method.

According to one embodiment of the invention, ALA is first ground and classified, the particle size range 90 to 160 μM being used. Freeze-dried Eudragit® NE (NE:carrier polymer) was dissolved together with acetyl tributyl citrate (ATBC; softener) in acetone, in an NE/ATBC ratio between 1:0.5 and 1:2.5. This was followed by the addition and dispersion of ALA in concentrations in the finished films of up to 50 wt. % (% g/g). The preparation was then drawn to produce a thin film on a cover foil and dried at 60° C. for 45 min. As a cover foil (or peel-off foil for the side of the film that comes into contact with the skin), Melinex 813 or a siliconised cover foil were found to be particularly suitable.

The adhesiveness of the film can be varied by the ALA content, the polymer used and the proportion of softener (in this case ATBC). The ALA release and its permeation through intact skin is influenced by ATBC (softener effect/permeation promotion effect).

In contrast to the conventional transdermal therapeutic systems (TTS), because of its high degree of hydrophily with all loads ≧approx. 1 wt. % (% g/g), ALA is mostly present suspended in the lipophilic NE/ATBC matrix.

Example 2

The ALA particles have a size of between approx. 90 and 160 μm and are homogenously distributed in the patch.

A homogenous distribution of the ALA particles in the finished patch requires a minimalisation of the sedimentation of the particles in the liquid polymer/softener/ALA preparation during the patch production. This is achieved by optimising the viscosity of the preparation by adjustment of the polymer concentration. The sedimentation behaviour of the ALA particles is reduced by an increase in viscosity.

| Concentration of NE [% g/g] in solution | Viscosity of the solution [mPas] | Sinking speed of the ALA particles* in solution [μm/10 s] |
|---|---|---|
| 12 | 446 | 396 |
| 18 | 2180 | 119 |
| 24 | 3510 | 3 |

*Sieve fraction 60-90 μm

An applied NE concentration of ≧25% g/g guarantees a minimum sedimentation speed of the ALA particles.

For other polymer matrices, i.e. other polymers, other ALA particle sizes may prove to be advantageous, which can be simply ascertained by the person skilled in the art in accordance with the available information and examples.

Example 3

ALA in the patch is stable in the long term.

The release of ALA/skin permeation from the patch directly after production and after 6-months' storage at 25° C. shows no essential differences (FIG. 1):

To determine the release profile, the patch is clamped in a Franz diffusion cell (cf. e.g. K. Tojo, "*Designated Calibration of in vitro Permeation Apparatus*" in "*Transdermal Controlled Systemic Medication*"; Y. Chien, Ed., Marcel Dekker, 1987) at 33° C. Samples of the aqueous acceptor solution are taken after various lengths of time and their ALA content determined by means of the fluorescence/derivatisation HPLC method.

Example 4

By use of a patch, ALA can be homogeneously applied to skin lesions.

The extremely easy handling of the patch systems represents an essential improvement for doctor and patient compared with ointment bases. A corresponding ALA-containing patch can be precisely trimmed to fit the area of skin to be treated. This reduces treatment of the surrounding area of skin which is not covered by the patch.

By application via a patch, the application is sharply delimited, without also penetrating surrounding regions of the skin.

After 3 hours' application of a patch loaded with 20% ALA (Eudragit® NE/acetyl tributyl citrate 1:1) on the forearm, the fluorescence of the skin area is measured. FIG. 2 shows that fluorescence is sharply delimited to the size of the patch and is homogeneous in appearance.

Example 5

Surprisingly, in contrast to conventional TTSs, a high proportion of the load of active substance is released within a very short time.

Conventional TTSs are loaded with a multiple of the dose of active substance actually required (Dittgen, M. "*Transdermale Therapeutische Systeme*" in "*Pharmaceutische Technologie; Moderne Arzneiformen*" ["Transdermal Therapeutic Systems" in "Pharmaceutical Technology; Modern drug forms"] Müller, R & Hildebrand, G., Ed.; Wissenschaftliche Verlagsgesellschaft Stuttgart, 1997). This excessive load is necessary, so that the active substance is released over a period of 1-7 days at an approximately constant rate by means of passive diffusion. During this application period, only a proportion <50% of the total active substance load is released.

Comparative Example 1

Scopolamine TTS (Ciba) is a membrane-controlled patch and contains a total of 1.5 mg Scopolamine. It releases 170 μg of Scopolamine per day, and is worn for three days. At the end of the third day approx. 30% of the total active substance load is therefore released.

Comparative Example 2

Estraderm TTS 25 (Geigy) is an adhesive membrane-controlled patch and contains a total of 2 mg of Estradiol. It releases 25 μg of Estradiol per day, and is worn for 3-4 days. During this application period, approx. 5% of the total active substance load is therefore released.

In contrast to conventional TTSs, surprisingly, the release of ALA from the NE/ATBC suspension patch was found to be extremely rapid. FIG. 3 shows the release profile for ALA, measured in vitro, from the 250 μm-thick patch of NE/ATBC (1:2.5) with a load of 20% g/g ALA (sieve fraction 90-160 μm). The plaster contained in total approx. 4 mg ALA/cm$^2$ and after 1 minute had already released more than 500 μg ALA (corresponding to 12.5% of the total active substance load). After 30 minutes, more than 1.3 mg ALA (corresponding to 32% of the total active substance load) had been released. The release profiles were carried out as described in Example 3.

The reason for this extremely rapid release is to be found in the particular construction/morphology of the dermal application system (suspension patch). Due to the presence of suspended ALA in the NE/ATBC matrix, 90 to 160 μm large ALA particles project partially through the surface of the ca. 250 μm thick matrix (cf. FIG. 4).

After brief contact with the aqueous release medium, the ALA particles projecting through the surface are no longer detectable (FIG. 5).

This unexpectedly rapid "surface decomposition" of the ALA particles is a direct consequence of their high level of hydrophily and leads to the extremely rapid release of the ALA from the patch observed (cf. FIG. 3).

Example 6

The time needed for the patch system to take effect for the photodynamic therapy (PDT) is approximately 30% shorter when compared with other applications using ointments or cremes.

Determination of the permeation of active substances through membranes of excised human stratum corneum/epidermis can be carried out using Franz cells and represents a suitable model for in vivo absorption through human skin. FIG. 6 shows the release/permeation profile for ALA from the NE/ATBC (1:2.0) patch with a film thickness of 250 μm and loaded with 20% ALA of the sieve fraction of 90 to 160 μm.

After 24 hours, approx. 300 μg ALA have already passed through human skin membrane. In comparison, FIGS. 7 and 8 show the distinctly lower release/permeation profiles of ALA from the ointment bases Psoralon-Fettcreme® (which contains 10 wt. % ALA) and hydroxyethyl cellulose gel (which contains 10 wt. % ALA).

From both these ointment bases, after 24 hours less than 10 μg ALA have passed through the human skin membrane. Clearly ALA is resorbed through the human skin membrane more rapidly and in greater quantities from the patch system. A comparison of the permeation rates makes this clear in quantitative terms:

| System/Base | Permeation rate [μg/cm$^2$/h] |
|---|---|
| NE/ATBC (1:2) patch | 12 |
| Psoralon-Fettcreme ® | 0.3 |
| hydroxyethyl cellulose gel | 0.18 |

A more rapid/stronger effect of the patch in comparison with the ointment base during in vivo PDT is therefore to be expected.

FIG. 9 shows the measured fluorescence intensity in healthy test subjects (forearm) depending on time. The intensity of the NE/ATBC (1:2) patch loaded with 20% ALA amounted after 2 hours to approx. 80% and after 3 hours to approx. 140% of a standard fluorescence preparation. A 50% ALA load of the patch, in comparison with 20% ALA load of the patch does not give any further increase in fluorescence intensity. The measured fluorescence intensity with Psoralon-Fettcreme® (20% ALA load) after an incubation period of 3 hours is distinctly lower (by approx. 60% than that from the NE/ATBC (1:2) patch (20% ALA load) worn for the same length of time (3 hours). With the application system according to the invention, distinctly shorter incubation (application) times can thus be achieved than with application forms such as ointments or creams.

The invention claimed is:

1. A dermal application system, which is a self-adhesive matrix system, consisting of aminolaevulinic acid (ALA) hydrochloride crystals suspended in a polymer matrix, wherein the polymer matrix consists of polymers from the group consisting of acrylates, and polyisobutylene, wherein a substantial amount of the ALA hydrochloride crystals have a mean diameter of 20 μm to 200 μm.

2. Application system according to claim 1, characterized in that the ALA hydrochloride crystals have a mean diameter of 30 μm to 190 μm.

3. Application system according to claim 2, characterized in that the ALA hydrochloride crystals have a mean diameter of 90 μm to 160 μm.

4. Application system according to claim 1, characterized in that the ALA hydrochloride is present in a concentration of 1 to 50 wt. % relative to the polymer matrix.

5. Application system according to claim 1, characterized in that it releases at least 30% of the ALA hydrochloride within 30 minutes.

* * * * *